United States Patent [19]

Fournet-Fayard et al.

[11] Patent Number: 5,486,174
[45] Date of Patent: Jan. 23, 1996

[54] FASTENER FOR THE OSTEOSYNTHESIS OF THE SPINAL COLUMN

[75] Inventors: Jacques Fournet-Fayard, Valence; Olivier Galland, Meylan; Christophe Garin, Lyons; Alain Lucet, Dijon, all of France

[73] Assignee: Soprane S.A., Lyons, France

[21] Appl. No.: 200,409

[22] Filed: Feb. 23, 1994

[30] Foreign Application Priority Data

Feb. 24, 1993 [FR] France ................................. 93 02357
Feb. 9, 1994 [FR] France ................................. 94 01661

[51] Int. Cl.$^6$ ............................ A61B 17/70; A61B 17/86
[52] U.S. Cl. ............................ 606/61; 606/73; 403/122
[58] Field of Search ........................ 606/61, 73; 403/122, 403/362, 52, 141, 143

[56] References Cited

U.S. PATENT DOCUMENTS

| | | | |
|---|---|---|---|
| 4,411,545 | 10/1983 | Roberge | 403/122 |
| 4,693,240 | 9/1987 | Evans | 403/362 |
| 5,042,982 | 8/1991 | Harms et al. | 606/61 |
| 5,176,680 | 1/1993 | Vignaud et al. | 606/61 |
| 5,209,751 | 5/1993 | Farris et al. | 606/61 |
| 5,306,275 | 4/1994 | Bryan | 606/61 |
| 5,352,226 | 10/1994 | Lin | 606/61 |

Primary Examiner—Stephen C. Pellegrino
Assistant Examiner—Scott B. Markow
Attorney, Agent, or Firm—Dowell & Dowell

[57] ABSTRACT

A fastener for relieving stress on a disc adjacent at least two vertebrae which are mechanically connected during osteosynthesis of the spinal column which fastener includes a fastening rod having a first portion which is secured to the at least two vertebrae by tightening elements provided on pedicle screws and a second portion, whose diameter is smaller than that of the first portion, which slides in a guidance element which is anchored in of the vertebra located adjacent the at least two vertebrae which are mechanically locked relative one another.

15 Claims, 4 Drawing Sheets

FASTENER FOR THE OSTEOSYNTHESIS OF THE SPINAL COLUMN

BACKGROUND OF THE INVENTION

1. Field of the Invention

The present invention relates to a fastener for lumbosacral osteosynthesis, making it possible to secure and assemble the damaged vertebral stages of this part of the spinal column.

2. History of the Related Art

We know of fasteners of this type which generally include two essentially parallel units, each comprising:

a cylindrical rod whose length is a function of the height and the number of vertebral stages to be joined;

and several units, each composed of a ring, a nut and a pedicle screw used for fastening the rods into the pedicles of each vertebra.

Such fasteners necessitate the alignment of the pedicle screws in the sagittal and frontal plane. Actually, if the alignment is not observed, the joining and connection by the rod is impossible, unless the rod is deformed so as to account for the angular displacement.

Moreover, the known fasteners have risks of a subsequent degeneration of the disc which lies immediately adjacent the assembly of mechanically locked or connected vertebrae. In effect, after the lumbosacral osteosynthesis, the disc receives all stresses which, in a normal state, are distributed to the several stages.

These are the drawbacks that the present invention intends to correct.

SUMMARY OF THE INVENTION

The fastener for lumbosacral osteosynthesis according to the present invention includes a fastening rod provided with a first part which cooperates with tightening devices provided on the pedicle screws and a second part having a smaller diameter than that of the first part which slides freely in the guidance means to relieve the stresses which are received by the disc of the vertebrae located just above the last vertebrae mechanically connected via the fastener.

BRIEF DESCRIPTION OF THE DRAWINGS

The attached drawings, provided as an example, will make it easier to understand the invention, the characteristics that it has and the advantages that it is capable of providing:

FIG. 1 shows the lower part of the spinal column (1) whose vertebrae (1a) are joined to one another by a fastener (2) in order to create a lumbosacral osteosynthesis, namely an interconnection of the vertebral stages of a portion of the spinal column.

Figure 1:
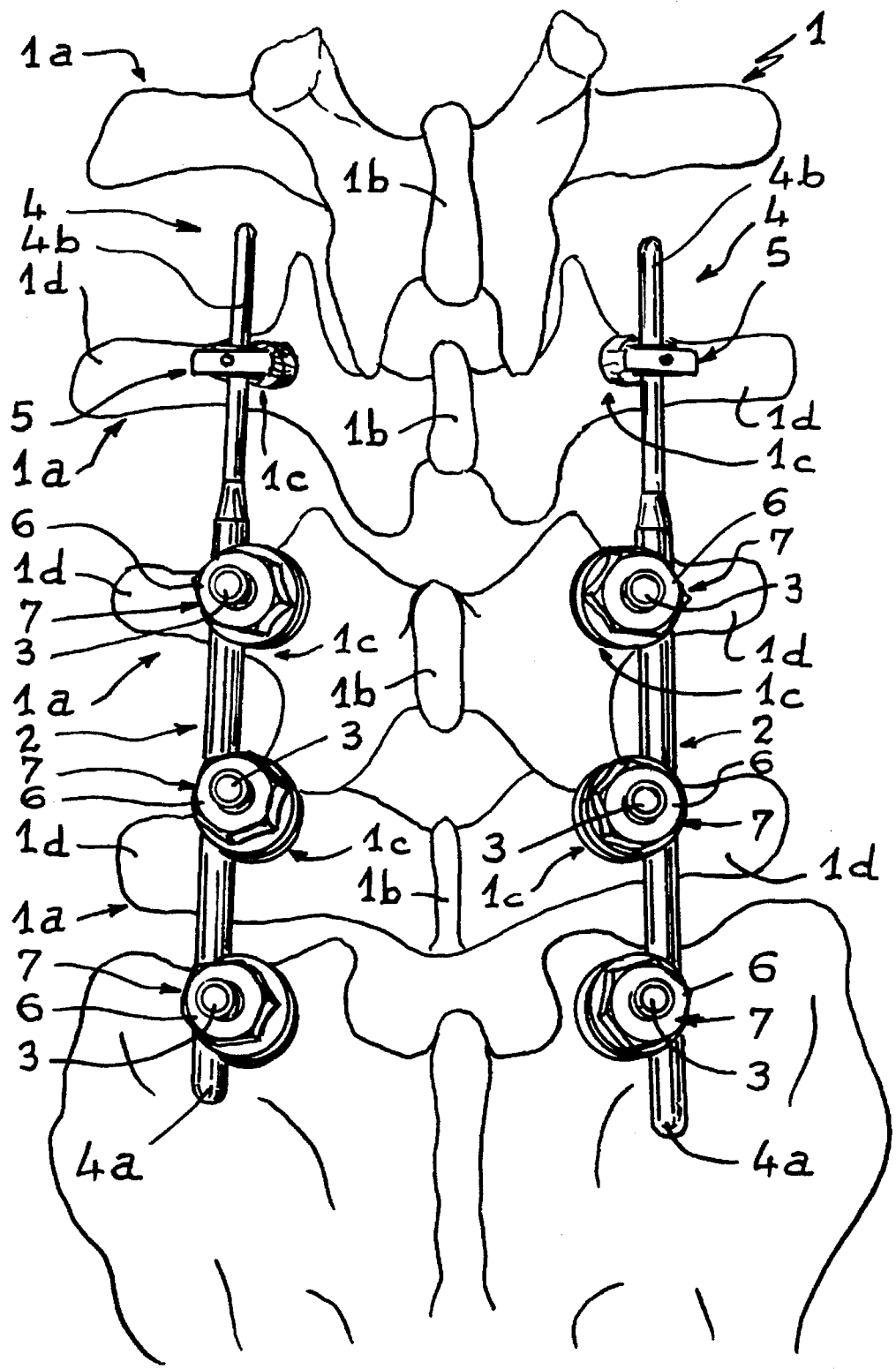
FIG. 1 is an elevated view illustrating the fastener for lumbosacral osteosyntheses according to the invention after it is put into place.

The fastener (2) includes two essentially parallel units which are placed on either side of the spine of vertebrae (1b) and locked on the pedicles (1c).

For each unit, the fastener (2) is made up of a certain number of pedicle screws (3) which are anchored in the pedicles (1c) of each vertebra (1a) and which comprise conventional tightening means (7), for securing a fastener rod (4). As shown, such a tightening means may include a nut (6) for tightening a ring member against the rod in a manner known within the art. The fastener rod (4) makes it possible to join each pedicle screw (3) previously anchored into the vertebrae (1a).

The cylindrical fastener rod (4) is generally supplied bent, either in a convex direction, or in a concave direction, according to the patient's morphology and the correction to be obtained. The rod (4) is provided with a sufficient length to connect a certain number of vertebrae (1a) whose discs are damaged.

The rod (4) has a first part (4a) which is provided to cooperate with the means (7) for tightening the pedicle screws (3) while the fastener (2) is being implanted.

The first part (4a) of the rod (4) is extended by a second part (4b) whose diameter is smaller. This second part (4b) may be provided, for example, to form a rod (4) having a uniform segmentation, i.e. the part (4a) is framed by two parts (4b) and, conversely, one part (4b) is framed by two parts (4a). The second part (4b) is designed to cooperate with guidance means (5) whose function will be described in more detail below. The guidance means (5) are installed on each transverse process (1d) of the vertebrae adjacent to the last mechanically locked or connected vertebrae, in order to create a semirigid transition between the normal vertebrae (1a) and that retained by the fastener (2) to prevent the creation of the "neo-hinge" syndrome.

Figure 2:
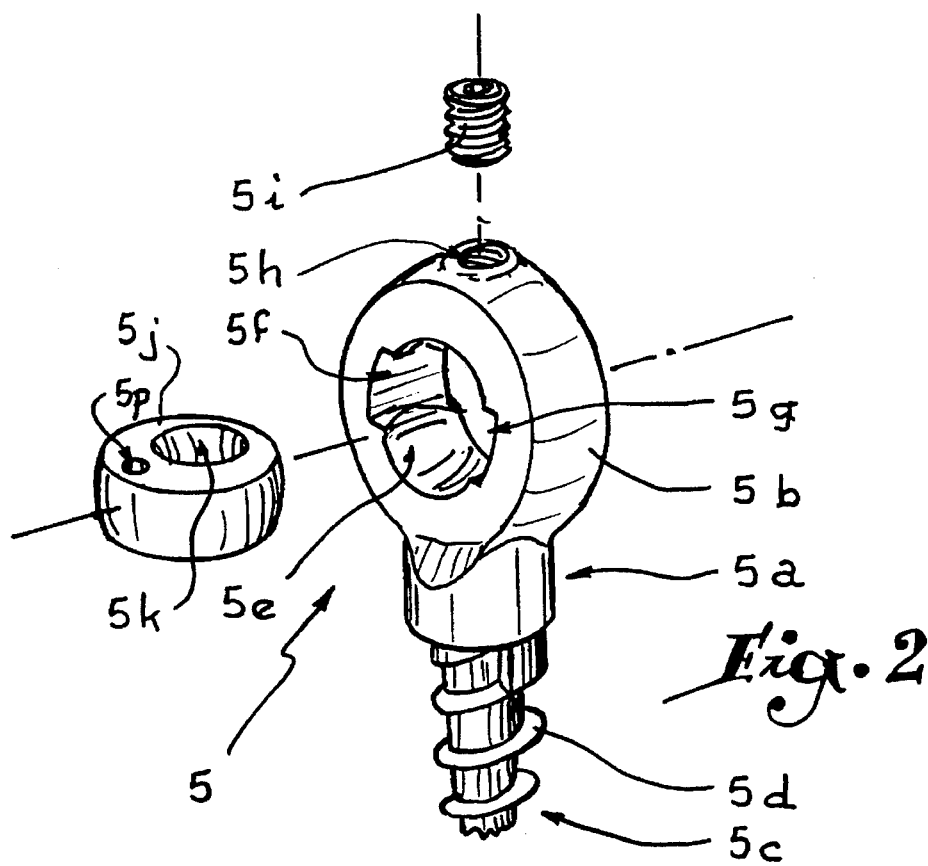
FIGS. 2 and 3 are perspective views of a guidance means which is designed to receive the second part of the fastener rod of the fastener according to the present invention.
Figure 3:
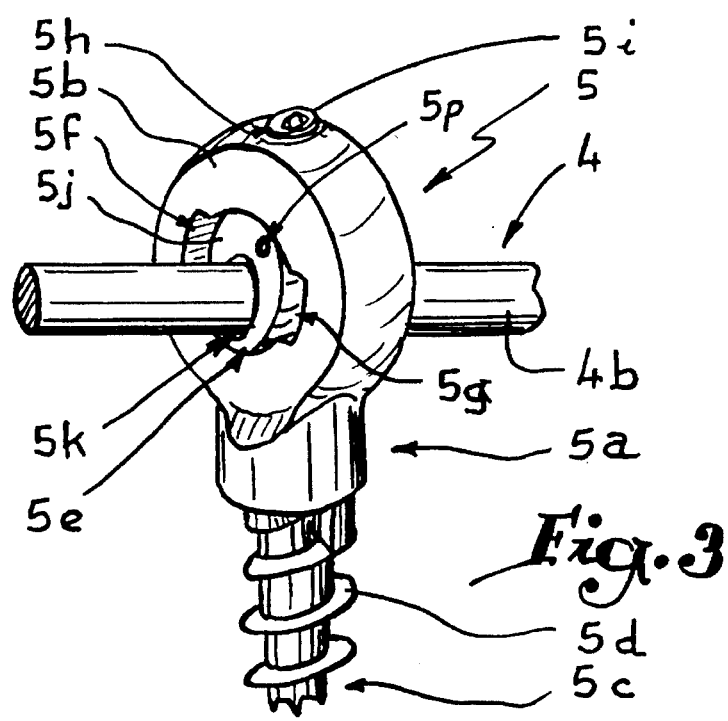
Figure 4:
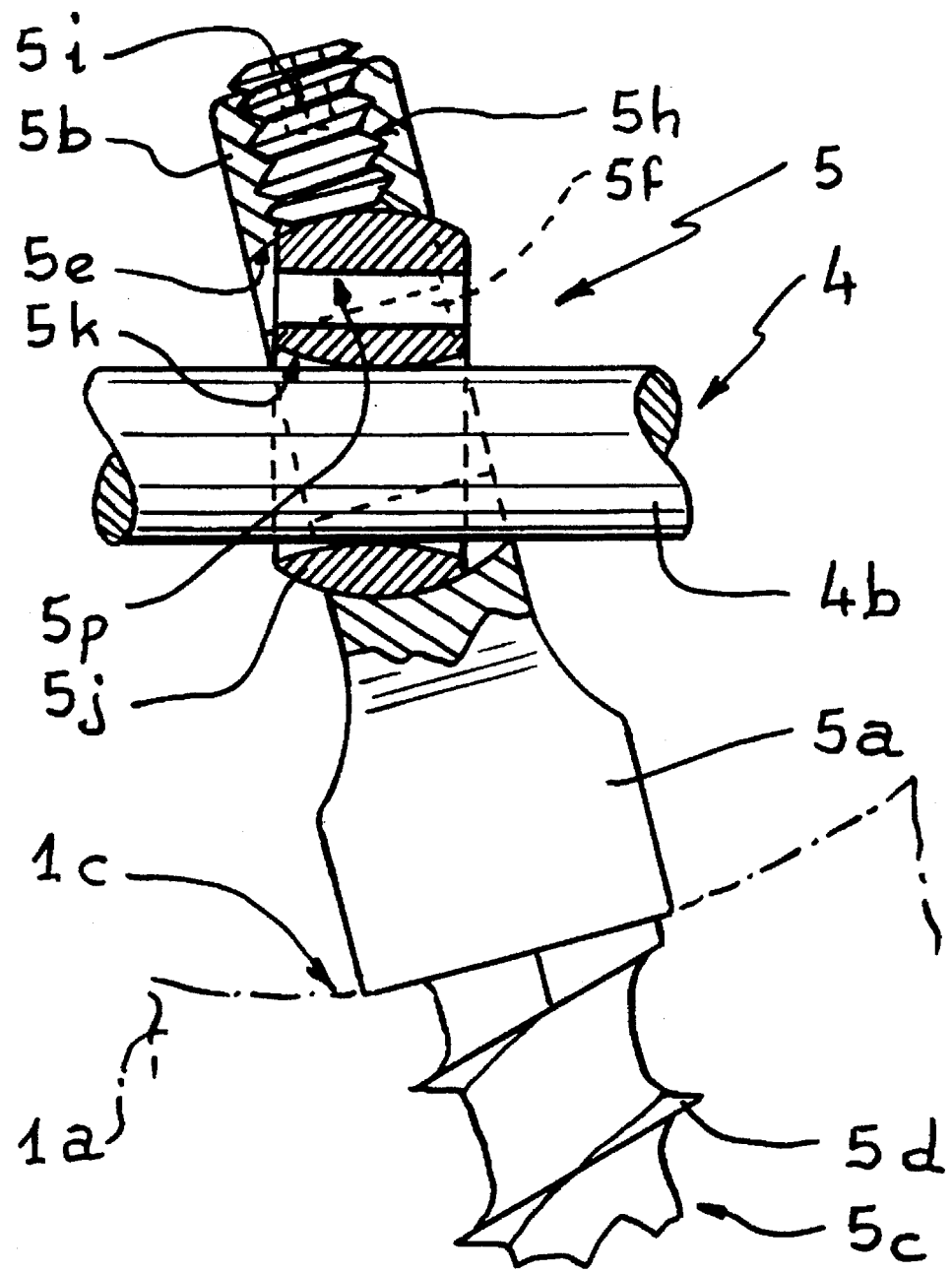
FIG. 4 is a sectional view illustrating the guidance of the second part of the fastener's fastening rod.

We have shown in FIGS. 2 through 4 the guidance means (5) for the second part (4b) of the fastening rod (4) in order to relieve the stresses which are received by the vertebral disc found just above the last connected vertebra (1a) using the fastener (2).

The guidance means (5) are made up of a screw (5a) whose head (5b) is ring-shaped. The screw (5a) comprises below its head (5b) a rod (5c) provided with a self-tapping thread (5d) allowing it to be anchored in the pedicle (1c) of the vertebra (1a) found above the last connected vertebra.

The head (5b) is open along a transverse axis relative to that of the rod (5c) to form a bore (5e) having an internal spherical profile. On either side of the bore (5e), two lateral notches (5f) and (5g) extend whose internal diameter is greater than that of the bore. In the upper part of the head (5b) and in alignment with the vertical axis of the screw, a tapped hole (5h) is provided which emerges inside of the bore (5g) and inside of which a screw (5i) is tightened.

A disk (5j) is introduced inside of the bore (5e) to form a ball-joint type link. The disk (5j) is provided with a first hole defining a guidance passageway (5k) which is angularly displaced relative to the main axis of the disk. The hole (5k) is defined by a rounded convex internal wall whose diameter is slightly larger than that of the part (4b) of the rod (4) so that the rod can slide freely inside of the disk (5j), as will be shown more clearly below. Additionally, the profile of the hole (5k) makes it possible to limit the surface in contact with part (4b) to reduce the friction stresses between the rod and the disk. A second hole (5p) is provided near hole (5k). It has a smaller diameter, allowing the surgeon to orient the disk (5j) inside the bore (5e) of the screw (5a). The disk (5j) has a spherical external profile whose radius is the same as that inside the bore (5e), so as to form a ball-joint type link allowing the disk (5j) to displace freely with different angular orientations inside of the bore (5e).

The rods (4), and more particularly their parts (4a), cooperate with the pedicle screws (3) previously anchored in the pedicles (1c) of each vertebra (1a) to be stress-relieved, whereas their parts (4b) cooperate with the ring screws (5) which are installed in each pedicle (1c) of the underlying vertebra (1a) to the last mechanically connected vertebra, in order to create a semirigid sliding connection between the normal vertebra (1a) and those retained by the fastener (2).

Before installing the screw-rings (5), the surgeon introduces the disk (5j) inside of the bore (5e) so that it remains in a free angular rotation. While introducing the rod (4), and more particularly part (4b), inside of the hole (5k) of the disk (5j), the surgeon displaces the latter angularly using an appropriate tool which cooperates with the hole (5p) in order to displace the disk in the proper direction as represented in FIG. 3. Then, the surgeon locks the disk (5j) inside the bore (5e) by means of screw (5i).

Figure 6:
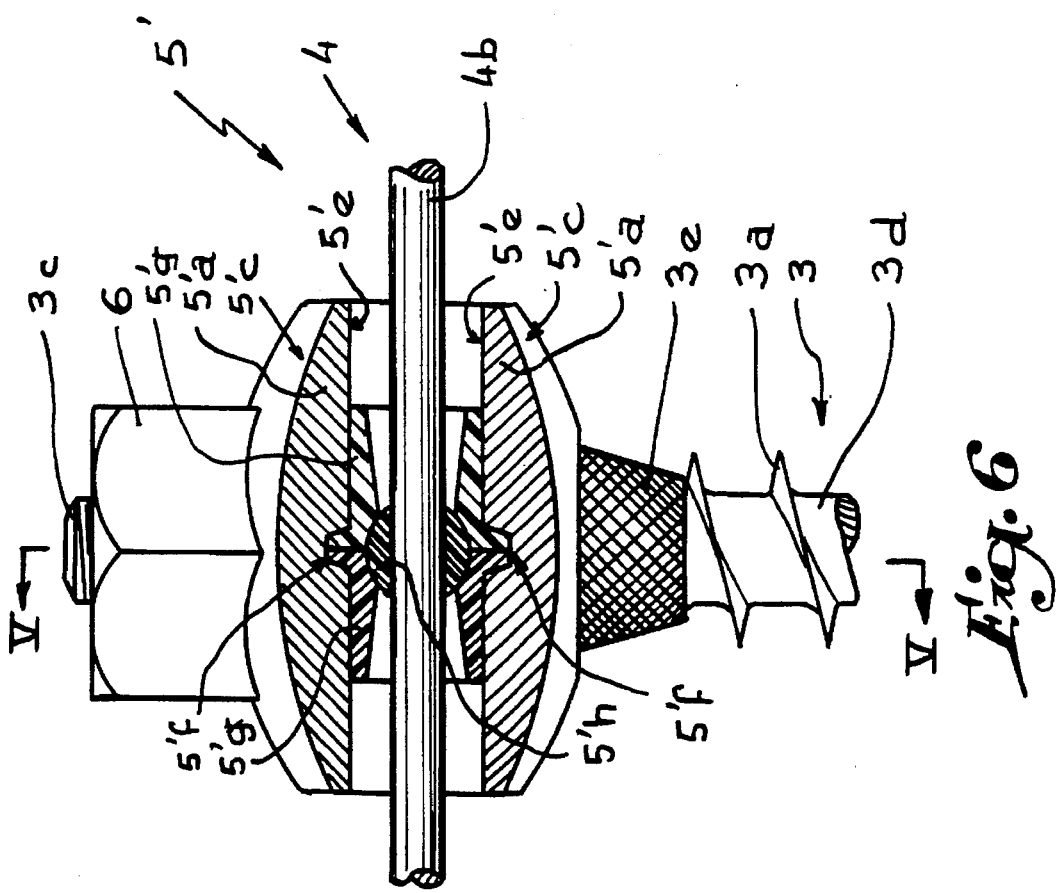
FIGS. 5 and 6 are sectional views showing variants of the guidance means of the second part of the fastening rod.
Figure 5:
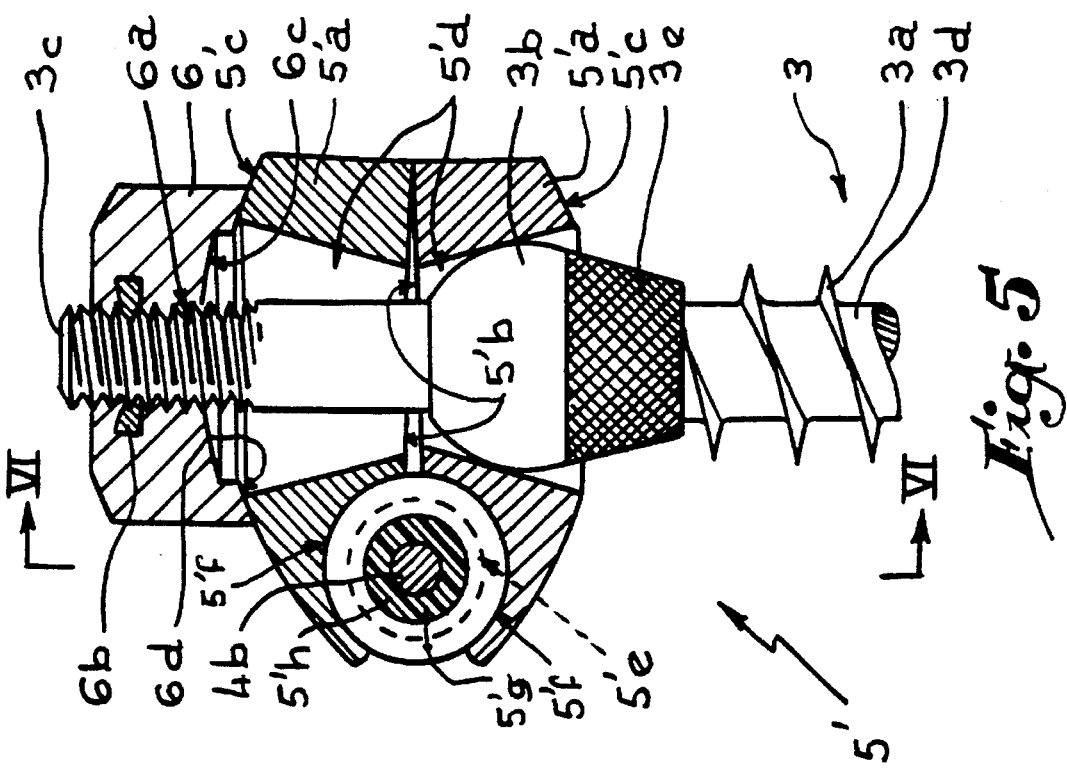

We have shown in FIGS. 5 and 6 one variant of the guidance means (3) referenced (5') of the second part (4b) of the fastener rod (4).

Guidance means (5') are installed on the pedicle screws (3) identical to those permitting the installation of part (4a) of the rod (4) and receiving tightening means (7), as described in FIG. 1.

Each pedicle screw (3) comprises a self-tapping thread (3a) and a spherical head (3b), the upper part of which is extended by a threaded rod (3c) coaxial to the thread (3a).

The self-tapping thread (3a) comprises a core (3d) with a conical profile to improve the stability of the upper part of the screw. The widest base of the conical profile of the bore (3d) is provided next to the spherical head (3b) of the pedicle screw (3).

The spherical head (3b) is extended next to the self-tapping thread (3a) by a conical part (3e) whose rough surface allows a gradual and lasting biological anchoring for the mending of the bone around the head.

The threaded rod (3c) is provided with a variable length along the anchoring point of the pedicle screw (3). Additionally, the threaded rod (3c) may be provided with rupture zones so that it can be divisible as a function of the height used.

The guidance means (5') are made up of two identical and symmetrical washers (5'a) capable of mutually forming either the lower part or the upper part of said guidance means. Each of the washers (5'a) has a flat bearing surface (5'b) and a semi-spherical exterior profile (5'c). Each washer (5'a) is provided with an open bore (5'd) which is displaced laterally relative to the vertical axis of the washers. The bore (5'd) has a conical profile whose widest base is turned next to the spherical profile (5'c) of the washers (5'a).

Notches (5'e) are provided perpendicular to the axis of the truncated bore (5'd) and comprise in their middle a V-groove (5'f). The latter permits the placement of nylon rings (5'g), in the middle of which a ball-joint (5'h) is provided having a through-bore for the sliding of the second part (4b) of the rod (4). The grooves (5'f) may be provided with any profile so that they retain the ring (5'g) axially in the rings (5'g). The washers (5'a) are locked to the pedicle screw (3) via a nut (6) comprising a tapped hole (6a) in which a stop washer (6b) is provided. Each nut is screwed to the threaded rod (3c) of the pedicle screws (3). Each nut (6) comprises a recess (6c) which makes it possible to delimit a semi-spherical surface (6d) on the bearing face of the nut. The spherical surface (6d) is provided with a radius corresponding to that of the profile (5'c) of the washers (5'a).

Note that the guidance means (5) and (5') create a semirigid transition between the normal vertebra (1a) and that retained or secured the fastener (2) to prevent the creation of the "neo-hinge" syndrome.

Moreover, it should be understood that the above description is provided solely as an example and that it does not limit in any way the scope of the invention from which we would not deviate by replacing the construction details described by all other equivalent details.

We claim:

1. A fastener for implanting to spaced vertebrate for relieving stress on a vertebral disc of a vertebral stage of patient's spinal column which is adjacent at least two vertebral stages which are mechanically united to one another and wherein each of the vertebral stages includes a vertebra having pedicles, the fastener comprising, a fastener rod having first and second portions, said second portion having a diameter which is less than the diameter of said first portion, at least two pedicle screw means, each pedicle screw means having a portion which is adapted to be anchorable into adjacent pedicles of the vertebrae of the at least two vertebral stages, each of said pedicle screw means including tightening means for securing said first portion of said rod to said at least two pedicle screw means so as to be in fixed relationship to the at least two vertebral stages when said fastener is in use, a guidance means having a screw portion which is adapted to be anchored into a pedicle of the vertebra of the next adjacent vertebral stage and a head portion, said head portion having an open passageway, said second portion of said fastener rod being continuously slidably engaged within said open passageway when said fastener is implanted in the vertebrae and said first portion of said rod is secured to said at least two pedicle screw means which are fixed to the at least two vertebral stages and said guidance means is secured to the next adjacent vertebral stage, whereby said fastener relieves stress on the disc adjacent the at least two vertebral stages when in use.

2. The fastener of claim 1 in which said head portion of said guidance means includes a bore having two lateral notches on opposite sides thereof, a disk mounted within said bore, said open passageway extending through said disk and means extending through said head portion for retaining said disk within said bore.

3. The fastener of claim 2 in which said bore has a spherical internal profile, and said means for retaining said disk within said bore includes an adjusting screw extending through said head portion.

4. The fastener of claim 3 in which said disk has an external profile complimentary to that of said bore so as to form a ball-joint like coupling.

5. The fastener of claim 4 in which said passageway includes an inner and rounded surface for reducing the area of contact and frictional resistance between said disk and said second portion of said fastener rod.

6. The fastener of claim 5 in which said disk includes a hole spaced from said passageway which is smaller in diameter than said passageway.

7. The fastener of claim 6 in which said screw portion includes a self-tapping thread.

8. The fastener of claim 1 in which said head portion includes a spherical head element which is generally coaxial to said screw portion, a pair of symmetrical washers each having a conically shaped open bore therethrough, said spherical head element being pivotably seated within said open bore of one of said washers, each of said washers including a notch which extends generally perpendicularly with respect to said open bore, said notches being in opposing relationship with respect to one another, ring means mounted between said notches, said ring having a ball-joint mounted therein, said open passageway extending through said ball-joint.

9. The fastener of claim 8 in which each of said notches includes a groove, said ring means including portions receivable within said grooves.

10. The fastener of claim 9 in which said grooves are v-shaped in profile.

11. The fastener of claim 8 in which said guidance means includes a threaded rod portion extending above said spherical head element, and a nut engageable with said threaded rod portion.

12. The fastener device of claim 11 in which each of said washers includes a flat inner bearing surface and an opposite semi-spherical outer surface, said nut having a lower semi-spherical surface which is engageable with the semi-spherical outer surface of one of said washers when said nut is threaded on said threaded rod portion of said guidance means.

13. The fastener device of claim 12 in which said spherical head element of said guidance means includes a conical portion having a roughened outer surface.

14. A fastener assembly for implanting to spaced vertebrae for relieving stress on a vertebral disc of a vertebral stage of patient's spinal column which is adjacent at least two vertebral stages which are mechanically united to one another and wherein each of the vertebral stages includes a vertebra having pedicles, the fastener assembly comprising, two essentially parallel fastener units, each of the units including a fastener rod and at least two pedicle screw means, each pedicle screw means having a portion which is adapted to be anchorable into adjacent pedicles of the vertebrae of the at least two vertebral stages, and each of the pedicle screw means including tightening means for securing said fastener rod to said at least two pedicle screw means so as to be in fixed relationship to the at least two vertebral stages, a pair of guidance means each having a screw portion which is anchorable into a pedicle of the vertebra of the next adjacent vertebral stage and a head portion, each head portion having an open passageway, each of said fastener rods being continuously slidably engaged with a separate one of said open passageways of said air of guidance means when said fastener assembly is implanted in the vertebrae and said first portion of said rods is secured to said at least two pedicle screw means of each of said fastener units which are fixed to the at least two vertebral stages and said pair of guidance means are secured to the next adjacent stage, whereby said fastener assembly relieves stress on the disc adjacent the at least two vertebral stages.

15. The fastener of claim 14 in which each of said fastener rods includes first and second portions, said second portion having a diameter which is less than the diameter of said first portion, said second portion of said fastener rods extending through said open passageway of said head portion of said guidance means.

* * * * *